(12) United States Patent
Otsubo

(10) Patent No.: US 7,000,764 B2
(45) Date of Patent: *Feb. 21, 2006

(54) PACKAGED DIAPERS ASSEMBLY

(75) Inventor: Toshifumi Otsubo, Kagawa (JP)

(73) Assignee: Uni-Charm Co., Ltd., Ehime-ken (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/735,835

(22) Filed: Dec. 16, 2003

(65) Prior Publication Data

US 2004/0173490 A1      Sep. 9, 2004

Related U.S. Application Data

(63) Continuation of application No. PCT/JP02/10021, filed on Sep. 27, 2002.

(30) Foreign Application Priority Data

Sep. 27, 2001   (JP)   ............................. 2001-297803

(51) Int. Cl.
*A61L 15/00* (2006.01)
(52) U.S. Cl. ................... 206/494; 206/440; 206/499
(58) Field of Classification Search ................ 206/440, 206/494, 497, 499, 507, 812; 53/429, 438; 221/48–54
See application file for complete search history.

(56) References Cited

U.S. PATENT DOCUMENTS

| | | | | |
|---|---|---|---|---|
| 3,367,489 A | * | 2/1968 | Schneider et al. | .......... 206/431 |
| 4,582,194 A | * | 4/1986 | Karpiloff et al. | ........... 206/485 |
| 5,022,216 A | * | 6/1991 | Muckenfuhs et al. | ......... 53/438 |
| 5,361,905 A | * | 11/1994 | McQueeny et al. | ......... 206/494 |
| 5,642,602 A | * | 7/1997 | Young et al. | .................. 53/438 |
| 5,927,498 A | * | 7/1999 | Saam | .......................... 206/499 |
| 5,934,470 A | * | 8/1999 | Bauer et al. | ................. 206/494 |
| 5,971,153 A | * | 10/1999 | Bauer et al. | ................. 206/494 |
| 6,079,562 A | * | 6/2000 | Bauer et al. | ................. 206/494 |
| 6,761,013 B1 | * | 7/2004 | Tippey et al. | ................. 53/429 |
| 2004/0195137 A1 | * | 10/2004 | Otsubo | ....................... 206/494 |

OTHER PUBLICATIONS

Patent Abstract of Japan; Publication No. 2000-042028 published Feb. 15, 2000 of Japanese Application No. 10-218999 filed Aug. 3, 1998.

(Continued)

*Primary Examiner*—David T. Fidei
(74) *Attorney, Agent, or Firm*—Lowe Hauptman & Berner, LLP

(57) ABSTRACT

A packaged assembly includes a package formed of in a rectangular hexahedron having first and second side walls opposed to each other and third and fourth side walls opposed to each other and a plurality of disposable diapers, each including a main body having an absorbent core attached thereto waist-surrounding peripheral end portions of the front and rear waist regions free from the absorbent core, packed within the package so that the plurality of disposable diapers may be stacked one upon another in a vertical direction of the package. The package contains therein first diapers each having the waist-surrounding peripheral end portions of the waist regions facing to the first side wall the package and second diapers each having the waist-surrounding peripheral end portions of the respective waist regions facing to the second side wall of the package and the plurality of diapers stacked one upon another in the vertical direction of the package constitute a group in which the number of the first diapers is equal to the number of the second diapers.

14 Claims, 5 Drawing Sheets

OTHER PUBLICATIONS

Patent Abstract of Japan; Publication No. 2000-042029 published Feb. 15, 2000 of Japanese Application No. 10-219000 filed Aug. 3, 1998.

Japanese Publication No. 2002-532350 published Oct. 2, 2002 of Japanese Application No. 2000-050 filed Dec. 14, 1999.

Japanese Publication No. 11-500988 published Jan. 26, 1999 of Japanese Application No. 9-523672 filed Dec. 9, 1996.

Japanese Publication No. 8-508455 published Sep. 10, 1996 of Japanese Application No. 6-522105 filed Mar. 16, 1994.

Japanese Publication No. 63-117779 published Jul. 29, 1988 of Japanese Application No. 62-9128 filed Jan. 23, 1987.

* cited by examiner

PACKAGED DIAPERS ASSEMBLY

This application is a continuation of International Application No. PCT/JP02/10021 filed Sep. 27, 2002, which claims priority to Japanese Application No. 2001-297803 filed Sep. 27, 2001.

BACKGROUND OF THE INVENTION

This invention relates to a packaged assembly consisting of a plurality of disposable diapers orderly packed within a package so that these diapers may be placed one upon another between both side walls opposed to each other.

Japanese Patent Application Publication No. 2000-42028A discloses a packaged assembly consisting of a plurality of pants-type disposable diapers orderly packed within a package each comprising a liquid-pervious topsheet, a liquid-impervious backsheet and a liquid-absorbent core disposed between these two sheets. Within the package, these diapers are arranged so that front waist regions are opposed to rear waist regions for respective pairs of the adjacent diapers. Each of these diapers packed in this manner, a crotch region is folded toward the rear waist region of this diaper. Within the package, waist-surrounding peripheral end portions of the front and rear waist regions of the respective diapers occupy an upper packaging space of the package and the remaining portions of the respective diapers except for the waist-surrounding peripheral end portions occupy the lower packaging space defined below the upper packaging space.

In most of the disposable diaper, the liquid-absorbent core does not extend to the waist-surrounding peripheral end portions of the front and rear waist regions and therefore the remaining portion of the diaper except for the waist-surrounding peripheral end portions has a thickness larger than that of those waist-surrounding peripheral end portions. Particularly when the crotch regions of the respective diapers are folded toward the respective rear waist regions to pack the diapers in this manner of the prior art, the thickness of the remaining portions except for the waist-surrounding peripheral end portions of the waist regions will be remarkably larger than the thickness of these waist-surrounding peripheral end portions. This will lead to a remarkably large difference of the thickness between the portion of the diapers occupying the upper packaging space of the package and the remaining portions of the diapers occupying the lower packaging space of the package.

According to the packaged assembly as disclosed in the above-cited Publication, a total thickness of a group of diapers placed one upon another between both side walls opposed to each other of the package is larger in the packaging lower space than in the upper packaging space of the package. In other words, even if the diapers are packed so as to occupy the maximum dimension between the both side walls opposed to each other of the package at its bottom, a gap will be left between each pair of the adjacent waist-surrounding peripheral end portions of the diapers in the upper packaging space of the package and efficiency for packing the diapers into the package will be deteriorated. Furthermore, this packaged assembly of the prior art is disadvantageous in that, when the groups of the diapers stacked vertically are packed in the package, the groups of the diapers occupying the upper packaging space of the package tend to flatten or collapse the waist-surrounding peripheral end portions of the diapers occupying the lower packaging space of the package and may form these waist-surrounding peripheral end portions of the diapers with a plurality of irregular wrinkles.

SUMMARY OF THE INVENTION

An principal object of this invention is to provide a packaged assembly consisting of a plurality of disposable diapers efficiently packed in a package without anxiety that the waist-surrounding peripheral end portions of the respective diapers might be formed with a plurality of irregular wrinkles.

According to this invention, there is provided a packaged diapers assembly comprising a package formed of a flexible sheet in a rectangular hexahedron having first and second side walls opposed to each other and a plurality of disposable diapers, each including a main body having an absorbent core attached thereto and respective waist-surrounding peripheral end portions of front and rear waist regions free from the absorbent core, packed within the package so that the disposable diapers are stacked one upon another in vertical direction of the package with the front and rear waist regions being opposed to each other in each of the diapers.

The package contains therein first diapers each having the waist-surrounding peripheral end portions of the respective waist regions facing to the first side wall of the package and second diapers each having the waist-surrounding peripheral end portions of the respective waist regions facing to the second side wall of the package and the plurality of diapers stacked in the vertical direction of the package constitute a group in which the number of the first diapers is equal to the number of the second diapers.

According to one preferred embodiment of this invention, a difference between the number of the first diapers and the number of the second diapers is in a range of 0–±3.

According to another preferred embodiment of this invention, the groups of at least two are arranged between the first and second side walls within the package.

According to still another preferred embodiment of this invention, the groups of at least two are packed side by side within the package.

DETAILED DESCRIPTION OF THE PREFERRED EMBODIMENTS

Details of the method according to this invention for orderly packing a plurality of diapers within a package will be more fully understood from the description given hereunder in reference to the accompanying drawings.

Figure 1:
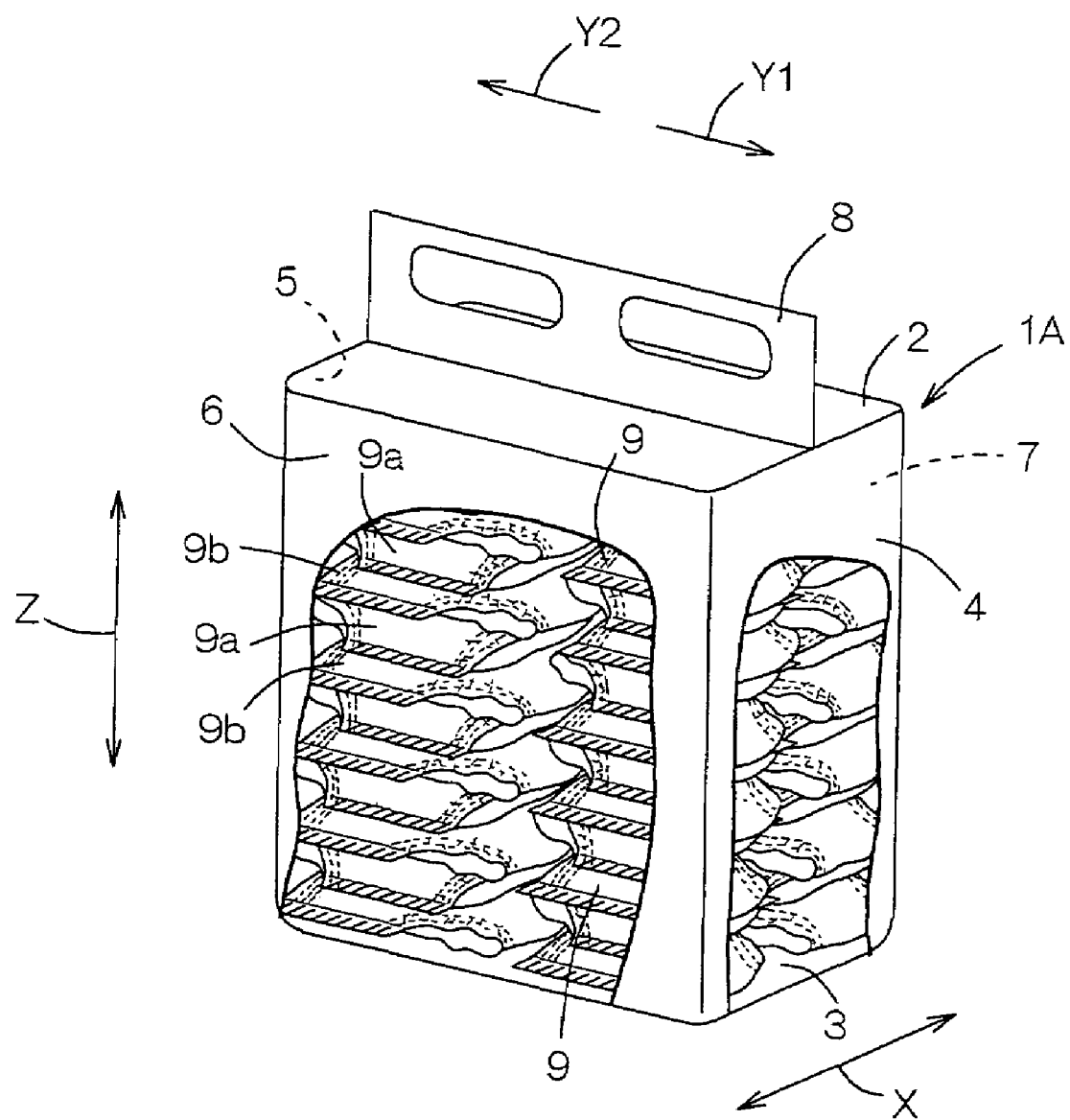
FIG. 1 is a partially cutaway perspective view showing a package.
Figure 2:
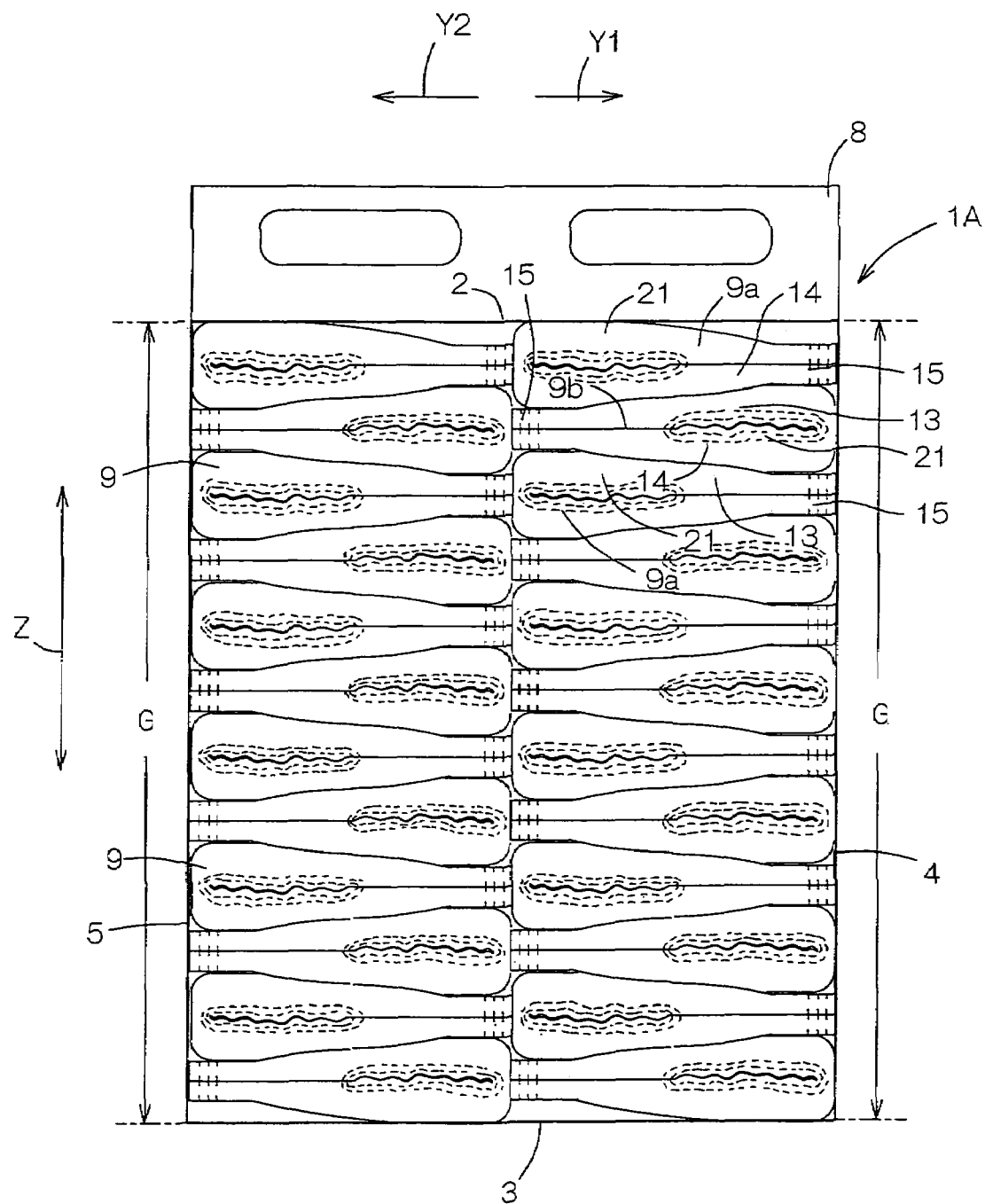
FIG. 2 is a side view showing the package as the diapers therein being exposed.
Figure 3:
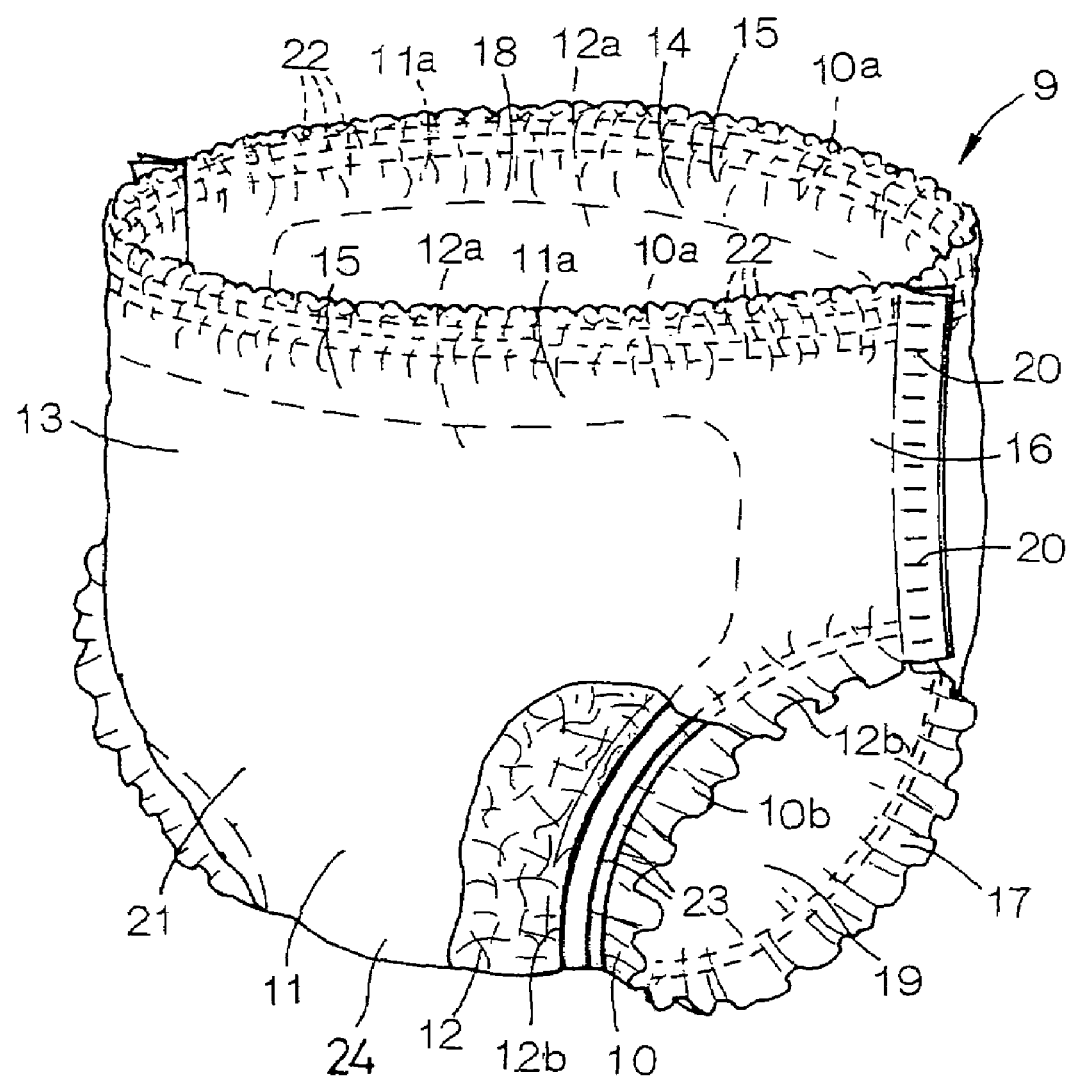
FIG. 3 is a partially cutaway perspective view showing the diaper as partially broken away.

FIG. 1 is a partially cutaway perspective view showing a package 1A, FIG. 2 is a side view showing the package 1A with a third side wall 6 cutaway to expose diapers 9 packed therein and FIG. 3 is a partially cutaway perspective view showing the individual diaper 9 taken out from the package 1A. In FIGS. 1 and 2, a transverse direction as viewed between third and fourth side walls 6, 7 a forward direction as viewed between first and second side walls 4, 5 is indicated by an arrow Y1, a backward direction as viewed between the first and second side walls 4, 5 is indicated by an arrow Y2 and a vertical direction is indicated by an arrow Z. Term "inner surfaces" of a topsheet 10 and a backsheet 11 used herein should be understood to mean respective surfaces thereof facing a liquid-absorbent core 12 (absorbent member) and term "outer surfaces" of these sheets 10, 11 should be understood to mean respective surfaces thereof facing away from the core 12.

This packaged assembly comprises the package 1A and the pants-type disposable diapers 9 orderly packed within the package 1A, wherein the diapers 9 are arranged within the package 1A for the maximum packing efficiency. In this packaged assembly, a plurality of the diapers 9 are packed within the package 1A so as to be stacked in the vertical direction under a compression.

The groups G each consisting of twelve diapers 9 stacked in the vertical direction are placed one upon another between the first and second side walls, as seen in FIG. 2. These two stacks of the groups G are placed side by side also within the package 1A, i.e., totally four groups G of the diapers 9 are packed within this package 1A.

The package 1A is formed of a flexible sheet in a rectangular hexahedron being relatively long in the vertical direction, in which each pair of adjacent surfaces are substantially orthogonal to each other. The package 1A comprises substantially rectangular top and bottom walls 2, 3 opposed to each other, substantially rectangular first and second side walls 4, 5 vertically extending between respective opposite ends of the top and bottom walls 2, 3, and substantially rectangular third and fourth side walls 6, 7 vertically extending between respective opposite side edges of the top and bottom walls 2, 3. The top wall 2 is provided with a handling projection 8 extending between first and second side walls 4, 5 of the package 1A.

As will be seen in FIG. 3, the diaper 9 comprises a liquid-pervious topsheet 10 facing a wearer's body, a liquid-impervious backsheet 11 facing away from the wearer's body and a liquid-absorbent core 12 interposed between these two sheets 10, 11. The core 12 is bonded to the inner surface of at least one of the top- and backsheets 10, 11.

The core 12 comprises a mixture of fluff pulp and super-absorbent polymer particles or a mixture of fluff pulp, super-absorbent polymer particles and thermoplastic synthetic resin fibers, in any case, compressed to a desired thickness. Necessarily, thickness of the core 12 is larger than those of the top- and backsheets. Preferably, the core 12 is entirely covered with a liquid-pervious sheet such as tissue paper or hydrophilic fibrous nonwoven fabric in order to prevent it from getting out of shape and/or to prevent the polymer particles from falling off.

The diaper 9 has front and rear waist regions 13, 14 opposed to each other. In the diaper 9, transversely opposite side portions 16 of the respective waist regions extending in the longitudinal direction are overlaid and joined to together in the vicinity of outermost edges of the respective side edge portions 16 by means of heat-sealing lines 20 arranged intermittently in the longitudinal direction. The diaper 9 is formed with a waist-hole 18 and a pair of leg-holes 19 lying below the waist-hole 18.

In the diaper 9, longitudinally opposite ends 12a of the core 12 lie inside waist-surrounding peripheral end portions 15 of the front and rear waist regions 13, 14 and transversely opposite side edges 12b of the core 12 lie inside the transversely opposite side portions 16 of the waist regions as well as thigh-surrounding peripheral end portions 17. In the diaper 9, the waist-surrounding peripheral end portions 15, the side portions 16 and the thigh-surrounding peripheral end portions 17 are free from the presence of the core 12, so a region 21 of the diaper 9 except these portions 15, 16, 17 has thickness larger than those of these portions 15, 16, 17. The individual diaper 9 is folded in two so that the front and rear waist regions 13, 14 may by placed upon each other as this diaper 9 is packed within the package 1A.

In the group G, first diapers 9a each having the waist-surrounding peripheral end portions 15 facing to the first side wall 4 and second diapers 9b each having the waist-surrounding peripheral end portions 15 facing to the second side wall 5 are alternately stacked in the vertical direction. In the group G, the number of the first diapers 9a is six and the number of the second diaper 9b is also six, that is, the number of the first and second diapers 9a, 9b are the same. From the top wall 2 toward the bottom wall 3 of the package 1A, the front waist region 13 of a second diaper 9b underlying a first diaper 9a is placed against the rear waist region 14 of this first diaper 9a and then the front waist region 13 of the next first diaper 9a underlying the next second diaper 9b is placed against the rear waist region 14 of this second diaper 9b, and so on.

In this packaged assembly, the first diapers 9a and the second diapers 9b are alternately stacked in the vertical direction and the number of the first diapers 9a is equal to the number of the second diapers 9b in the group G. Therefore, the thickness of the group G in the vertical direction has substantially no difference between its front half and rear half in spite of the fact that, both in the first diapers 9a and in the second diapers 9b, the thickness of the main body 21 is larger than the thickness of the waist-surrounding peripheral end portions 15. Even when the diapers 9 are packed within the package 1A to fill the maximum dimension of the package 1A in the vertical direction, no gap is formed between each pair of the adjacent diapers 9 both in the front half and in the rear half of the group G and thereby a packing efficiency for the diapers 9 within the package 1A can be improved.

In this packaged assembly, the first diapers 9a and the second diapers 9b in the group G are stacked in the vertical direction in sufficiently close contact one with another to prevent the waist-surrounding peripheral end portions 15 of the diapers 9 from being easily folded. Therefore, even when the groups G each stacked in vertical direction are packed within the package 1A not only between the first and second side walls 4, 5 between the third and fourth side walls 6, 7, it is not apprehended that the group(s) G of the diapers 9 might collapse the waist-surrounding peripheral portions 15 of the diapers 9 in the adjacent group(s) G and consequently form the waist-surrounding peripheral end portions 15 of the diapers 9 with a plurality of irregular wrinkles.

Along the waist-surrounding peripheral end portions 15 of the diaper 9, respective end portions 10a, 11a of the top- and backsheets 10, 11 extending outward beyond longitudinally opposite ends 12a of the core 12 are overlaid and joined together. The waist-surrounding peripheral end portions 15 of the diaper 9 are provided with waist-surrounding elastic members 22 secured thereto in a stretched state. These waist-surrounding elastic members 22 are interposed between the top- and backsheets 10, 11 and bonded to respective inner surfaces of the end portions 10a, 11a of these sheets 10, 11.

Along the transversely opposite side portions 16 of the waist regions and thigh-surrounding peripheral end portions 17, respective side edge portions 10b, 11b of the top- and backsheets 10, 11 extending outward beyond transversely opposite side edges 12b of the core 12 are overlaid and joined together. The thigh-surrounding peripheral end portions 17 of the diaper 9 are provided with thigh-surrounding elastic members 23 secured thereto in a stretched state. These thigh-surrounding elastic members 23 are interposed between the top- and backsheets 10, 11 and bonded to respective inner surfaces of the side edge portions 10b, 11b of these sheets 10, 11.

Figure 4:
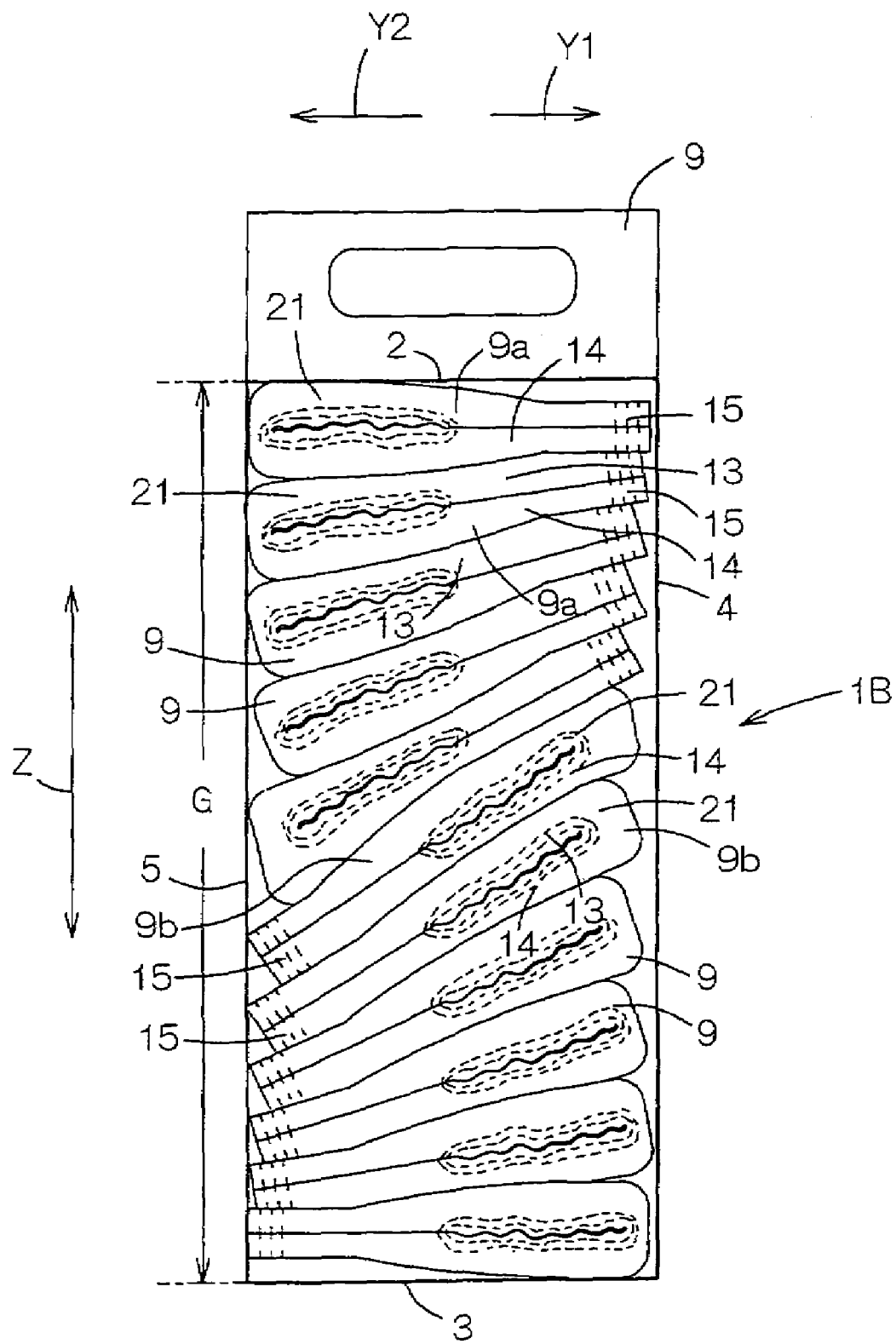
FIG. 4 is a side view of a package illustrating one preferred embodiment of the packaged assembly comprising the diapers orderly packed within the package.
Figure 5:
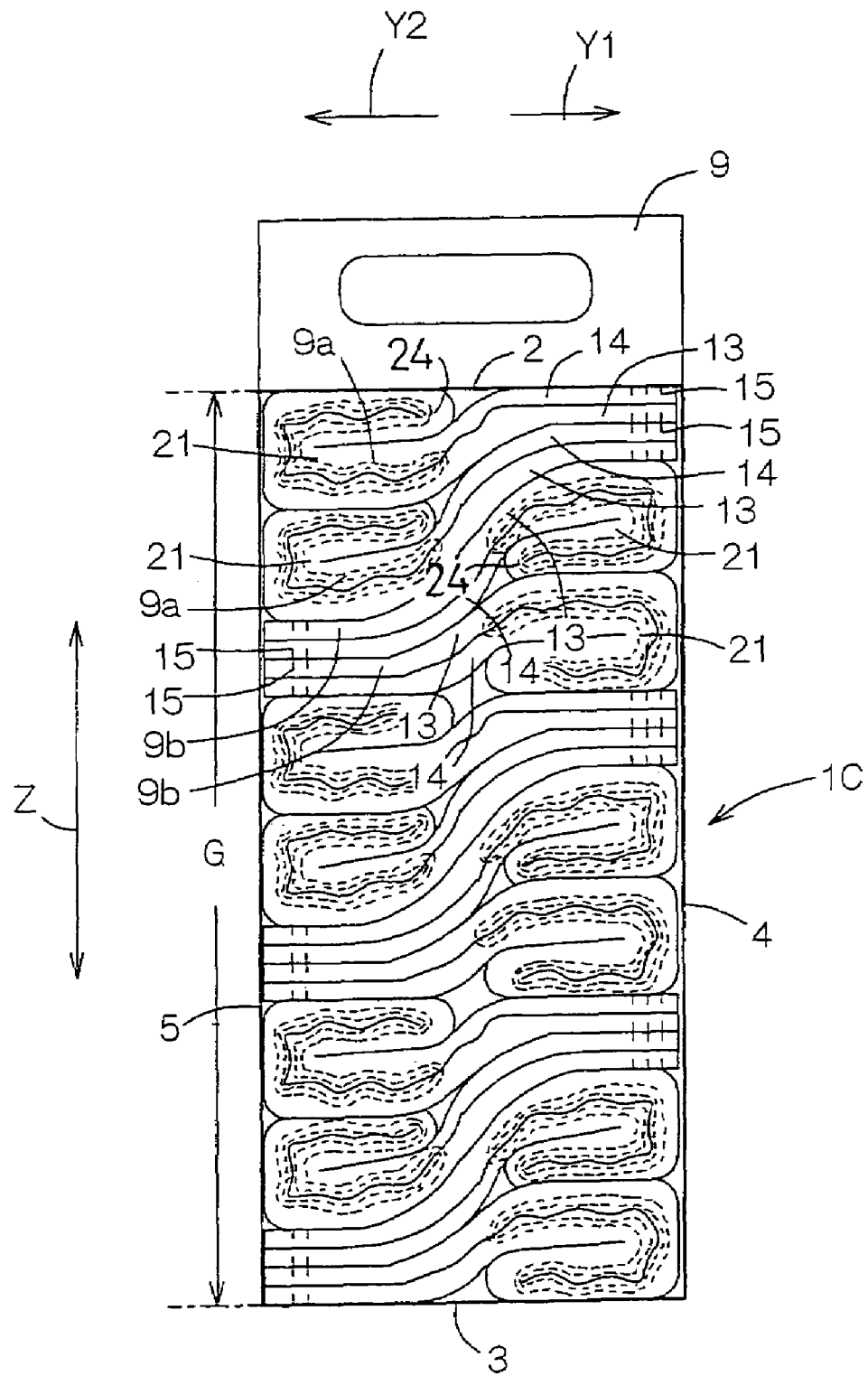
FIG. 5 is a side view of a package illustrating another preferred embodiment of the packaged assembly comprising the diapers orderly packed within the package.

FIG. 4 is a side view of a package 1B illustrating one preferred embodiment of the packaged assembly and FIG. 5 is a side view of the package 1C illustrating another preferred embodiment of the packaged assembly. FIGS. 4 and 5 show the packages 1B, 1C with the third side walls 6 thereof cutaway to expose the diapers 9 packed therein. In FIGS. 4 and 5, a forward direction is indicated by an arrow Y1, a backward direction is indicated by an arrow Y2 and a vertical direction is indicated by an arrow Z.

Similarly to the package 1A shown in FIG. 1, each of packages 1B, 1C is formed of a flexible sheet in a rectangular hexahedron being relatively long in the vertical direction in which each pair of adjacent surfaces are substantially orthogonal to each other. The diaper 9 is the pants-type disposable diaper 9 similar to that shown in FIG. 1 and the main body 21 which is the region of the diaper 9 except for the waist-surrounding peripheral end portions 15, the transversely opposite side portions 16 of the waist regions and the thigh-surrounding peripheral end portions 17 has the thickness larger than those of these portions 15, 16, 17. The individual diapers 9 are folded so that the front and rear waist regions 13, 14 thereof may contact each other as these diapers 9 are packed within the package 1B, 1C.

The packaged assemblies shown in FIGS. 4 and 5, respectively, are distinguished from the packaged assembly shown in FIG. 1 in arrangement as will be described. In the packaged assembly shown in FIG. 4, one group G consists of eleven diapers 9 stacked in the vertical direction of the package 1B. In the packaged assembly shown in FIG. 5, one group G consists of twelve diapers 9 stacked in the vertical direction of the package 1C. Within these packages 1B, 1C, these diapers 13 are under compression in the vertical direction.

Referring to FIG. 4, the group G comprises five first diapers 9a and six second diapers 9b. In the group G, the first diapers 9a are stacked in the vertical direction from a vertically middle of the package 1B toward the top wall 2 of the package 1B and the second diapers 9 are stacked in the vertical direction from the bottom 3 of the package 1B toward the vertically middle of the package 1B.

The waist-surrounding peripheral end portions 15 of the first diaper 9a face to the first side wall 4. The waist-surrounding peripheral end portions 15 of the second diaper 9b facing to the second sidewall 5. Concerning the first diapers 9a arranged from the vertically middle of the package 1B toward the top wall 2 of the package 1B, the front waist region 13 of the diaper 9a underlying the uppermost first diaper 9a is placed against the rear waist region 14 of this uppermost first diaper 9a and the front waist region 13 of the first diaper 9a underlying this precedent first diaper 9a is placed against the rear waist region 14 of this precedent first diaper 9a, and so on. Concerning the second diapers 9b stacked from the bottom wall 3 of the package 1B toward the vertically middle of the package 1B, the front waist region 13 of the diaper 9b underlying the uppermost second diaper 9b is placed against the rear waist region 14 of this uppermost second diaper 9b and the front waist region 13 of the second diaper 9b underlying this precedent second diaper 9b is placed against the rear waist region 14 of this precedent second diaper 9b, and so on.

In the packaged assembly shown in FIG. 4, the number of the second diapers 9b is larger than the number of the first diapers 9a by one in the group G. In spite of this difference in the number of the first and second diapers 9a, 9b, there is no anxiety that a gap might be formed between each pair of the adjacent diapers 9 both at the side of the first side wall 4 and at the side of the second side wall 5 of the group G because the thickness of the group G in the vertical direction in the vicinity of the first side wall 4 of the package 1B is substantially equal to that in the vicinity of the second side wall 5 of the package 1B. In this way, a packing efficiency for the diapers 9 within the package 1B is improved.

Referring to FIG. 5, each of the group G consists of six first diapers 9a and six second diapers 9b. In the group G, each pair of the first diapers 9a are stacked upon each other in the vertical direction and each pair of the second diapers 9b are stacked upon each other in the vertical direction. In this manner, the pair of the first diapers 9a and the pair of the second diapers 9b are alternately stacked in the vertical direction.

Concerning the first diaper 9a, a crotch region 24 is folded toward the outer surface of the backsheet 11 extending in the rear waist region 14 and the waist-surrounding peripheral end portions 15 face to the first side wall 4. Concerning the second diaper 9b, the crotch region 24 is folded toward the outer surface of the backsheet 11 extending in the rear waist region 14 and the waist-surrounding peripheral end portions 15 face to the second side wall 5. In each pair of the first diapers 9a, the front waist region 13 of the lower diaper 9a is placed against the rear waist region 14 of the upper diaper 9a. In each pair of the second diapers 9b, the rear waist region 14 of the lower diaper 9b is placed against the front waist region 13 of the upper diaper 9b. The front waist region 13 of the first diaper 9a and the front waist region 13 of the second diaper 9b are placed upon each other.

In the packaged assembly shown in FIG. 5, the number of the first diapers 9a is equal to the number of the second diapers 9b and there is no difference in the thickness of the package 1C in the vertical direction between in the vicinity of the first side wall 4 and in the vicinity of the second side wall 5 of the package 1C. In this packaged assembly, no gap is formed between each pair of the adjacent diapers between the first and second side walls 4, 5 of the package 1C and a packing efficiency for the diapers 9 within the package 1C is effectively improved.

The packaged assembly shown in FIG. 5 may be modified so that a set of three or more first diapers 9a and a set of three or more second diapers 9b are alternately stacked one upon another in the vertical direction. In the packaged assembly shown in FIG. 5, it is not essential to fold the crotch regions 24 of the diapers 9.

For these packaged assemblies as have been described above, a difference in the number of the first diapers 9a and the number of the second diapers 9b in one and same group G is preferably in a range of 0–±3. In any one of these embodiments, three or more groups G may be arranged between the first and second side walls 4, 5 and/or three or more groups G may be arranged between the third and fourth side walls 6, 7 within the package 1A, 1B, 1C. The diapers packed within the package 1A, 1B, 1C are not limited to the pants-type diaper but may be open-type diapers having transversely opposite side edge portions of the front and rear waist regions being connected as the diapers are worn. The number of the diapers 9 packed within the package 1A, 1B, 1C is not specified and may be increased to thirteen or more or reduced to nine or less.

The package 1A, 1B, 1C may be formed using a breathable but liquid-impervious plastic film or a breathable but liquid-impervious fibrous nonwoven fabric. The topsheet 10 of the diaper 9 may be formed using a hydrophilic fibrous nonwoven fabric, a hydrophobic fibrous nonwoven fabric having a plurality of fine pores or a plastic film having a plurality of fine pores. The backsheet 11 of the diaper 9 may be formed using a hydrophobic fibrous nonwoven fabric, a breathable but liquid-impervious plastic film, a composite nonwoven fabric consisting of layers of hydrophobic fibrous nonwoven fabrics laminated one with another or a composite sheet consisting of a hydrophobic fibrous nonwoven fabric and a breathable but liquid-impervious plastic film.

The plastic film used herein is preferably made of polyolefine-based thermoplastic synthetic resin such as polypropylene or polyethylene.

The fibrous nonwoven fabric used herein may be selected from a group including products obtained by spun lace process, needle punch process, melt blown process, thermal bond process, spun bond process, chemical bond process and air-through process. Component fiber of the nonwoven fabric may be selected from a group including polyolefine-, polyester-, polyamide-based fibers and core-sheath type or side-by-side type conjugated fibers of polyethylene/polypropylene or polyethylene/polyester.

The packaged assembly according to this invention has the advantageous effects that a plurality of diapers comprising the first diapers each having the waist-surrounding peripheral end portions facing to the first side wall 4 of the package and the second diapers each having the waist-surrounding peripheral end portions facing to the second side wall 5 of the package are packed within the package and each group of the diapers consists of the first and second diapers of approximately same number. Even if a plurality of the diapers each having different thickness between the waist-surrounding peripheral end portions and the main body are packed within the package so as to fill the maximum dimension of the package in its vertical direction, no gap will be formed between each pair of the adjacent diapers both at the side of the first side wall 4 and at the side of the second side wall 5 of the group. In this way, a packing efficiency for the diapers within the package is improved.

With this packaged assembly, the first and second diapers are stacked one upon another in sufficiently close contact one with another in the vertical direction to prevent the waist-surrounding peripheral end portions to be easily folded. Therefore, even when two or more groups are arranged between the first and second side walls 4, 5 as well as between the third and fourth side walls 6, 7 within the package, it is not apprehended that the one group(s) of the diapers might collapse the waist-surrounding peripheral portions of the diapers in the other group(s) and consequently form the waist-surrounding peripheral end portions of the diapers in the adjacent group(s) with a plurality of irregular wrinkles.

Even when the number of the first diapers is not equal to the number of the second diapers in one and same group, no gap will be formed between each pair of the stacking diapers both at the side of the first side wall 4 and at the side of the second side wall 5 of the group so far as the difference between these numbers is in a range of 0–±3. In this way, a packing efficiency for the diapers within the package is improved.

What is claimed is:

1. A packaged assembly, comprising
a package formed of a flexible sheet in a rectangular hexahedron having a top wall, a bottom wall, and first and second side walls being opposed to each other and connecting the top and bottom walls, said package further comprising a handle at the top wall; and
a plurality of disposable diapers, each including a main body having an absorbent core attached thereto and respective waist-surrounding peripheral end portions of front and rear waist regions free of the absorbent core, said diapers being packed within said package so that said disposable diapers are stacked one upon another in a vertical direction between said top and bottom walls of said package with said front and rear waist regions in each of the diapers being placed one atop another;
wherein
said diapers comprise first diapers each having said waist-surrounding peripheral end portions of the respective waist regions facing to said first side wall of said package and second diapers each having said waist-surrounding peripheral end portions of the respective waist regions facing to said second side wall of said package; and
said plurality of diapers are stacked in said vertical direction of said package to constitute at least one column which extends from the top wall to the bottom wall and in which the number of said first diapers is substantially equal to the number of said second diapers.

2. The packaged assembly according to claim 1, wherein a difference between the number of said first diapers and the number of said second diapers is in a range of 0–±3.

3. The packaged assembly according to claim 1, wherein said at least one column includes two or more columns arranged between said first and second side walls within said package.

4. The packaged assembly according to claim 1, wherein said at least one column includes two or more columns packed side by side within said package.

5. The packaged assembly according to claim 4, wherein said diapers are stored in said each of said columns in a compressed state between said top and bottom walls of said package.

6. The packaged assembly according to claim 4, wherein four of said columns are packed side by side within said package.

7. A package of disposable diapers, comprising:
a flexible container comprising a top wall, a bottom wall, and first and second opposing side walls that connect the top and bottom walls, said container further comprising a handle at the top wall; and
a plurality of disposable diapers packed within said container, each of said diapers including front and rear waist regions, which define together a waist hole, and a crotch region extending between said front and rear waist regions and being opposed to the waist opening;
wherein
said diapers are stacked one upon another, with said front and rear waist regions of each of the diapers being placed one atop another, to define at least one column of diapers extending in a vertical direction from said top wall to said bottom wall;
said diapers comprise first diapers having the waist holes facing the first side wall and second diapers having the waist holes facing the second side wall, wherein said first and second diapers are alternatively arranged in said column.

8. The package of claim 7, wherein said container has a shape of a substantially rectangular hexahedron having adjacent surfaces being substantially orthogonal with each other.

9. The package of claim 7, wherein each of said diapers comprises a liquid-pervious topsheet, a liquid-impervious backsheet and a liquid-absorbent core interposed between said topsheet and backsheet and extending between said front and rear waist regions.

10. The package of claim 7, wherein a difference between a number of said first diapers and a number of said second diapers in said column is in a range of 0–3.

11. The package of claim 7, comprising at least two said columns being placed side by side.

12. The package of claim 11, comprising four said columns.

13. The package according to claim 12, wherein each of said diapers is a pants-type diaper having transversely opposite lateral portions of the front and rear waist regions being permanently attached to each other.

14. The package of claim 7, wherein said diapers are stored in said column in a compressed state between said top and bottom walls of said container.

* * * * *